(12) United States Patent
Crisp et al.

(10) Patent No.: US 6,522,918 B1
(45) Date of Patent: Feb. 18, 2003

(54) ELECTROLYTIC DEVICE

(76) Inventors: William E. Crisp, 6051 Cactus Wren Rd., Paradise Valley, AZ (US) 85253-4238; Javin Pierce, 4780 Mountain Rd., Stowe, VT (US) 05672

( * ) Notice: Subject to any disclaimer, the term of this patent is extended or adjusted under 35 U.S.C. 154(b) by 0 days.

(21) Appl. No.: 09/499,932

(22) Filed: Feb. 9, 2000

(51) Int. Cl.⁷ .................................................. A61N 1/30
(52) U.S. Cl. .......................................... 604/20; 604/46
(58) Field of Search ............................ 604/19, 20, 174, 604/289–291, 46, 501

(56) References Cited

U.S. PATENT DOCUMENTS

| | | | |
|---|---|---|---|
| 222,276 A | 12/1879 | Hunter | |
| 527,037 A | 10/1894 | Funk | |
| 3,964,477 A | * 6/1976 | Ellis et al. | 604/20 |
| 4,034,750 A | 7/1977 | Seiderman | 128/155 |
| 4,241,105 A | 12/1980 | Mayweather | 427/125 |
| 4,528,265 A | 7/1985 | Becker | 435/172.1 |
| 4,767,401 A | 8/1988 | Seiderman | 604/20 |
| 4,919,648 A | * 4/1990 | Sibalis | 604/20 |
| 4,927,408 A | 5/1990 | Haak et al. | 604/20 |
| 5,084,006 A | 1/1992 | Lew et al. | 604/20 |
| 5,084,008 A | * 1/1992 | Phipps | 604/20 |
| 5,162,042 A | 11/1992 | Gyory et al. | 604/20 |
| 5,203,768 A | 4/1993 | Haak et al. | 604/20 |
| 5,288,289 A | 2/1994 | Haak et al. | 604/20 |
| 5,298,017 A | 3/1994 | Theeuwes et al. | 604/20 |
| 5,322,520 A | 6/1994 | Milder | 604/265 |
| 5,395,398 A | 3/1995 | Rogozinkski | 607/50 |
| 5,405,317 A | 4/1995 | Myers et al. | 604/20 |
| 5,503,840 A | 4/1996 | Jacobson et al. | 424/421 |
| 5,549,640 A | 8/1996 | Fontenot | 607/149 |
| 5,668,170 A | 9/1997 | Gyory | 514/449 |
| 5,685,837 A | 11/1997 | Horstmann | 604/20 |
| 5,741,224 A | * 4/1998 | Milder et al. | 604/20 |
| 5,782,788 A | 7/1998 | Widemire | 602/48 |
| 5,814,094 A | 9/1998 | Becker et al. | 607/50 |
| 5,911,223 A | * 6/1999 | Weaver et al. | 604/20 |

* cited by examiner

Primary Examiner—J. Casimer Jacyna
(74) Attorney, Agent, or Firm—Downs Rachlin Martin PLLC

(57) ABSTRACT

An electrolytic device (20) comprising a structure (22) having a first surface (24) with a first surface area, a thickness region (29) and a plurality of openings (30) in the thickness region. The plurality of openings (30) is defined by a plurality of inner surfaces (34) that together have an inner surface area. The plurality of inner surfaces comprise silver. A metal-bearing material (40) other than silver is interspersed throughout at least some of the plurality of openings.

36 Claims, 8 Drawing Sheets

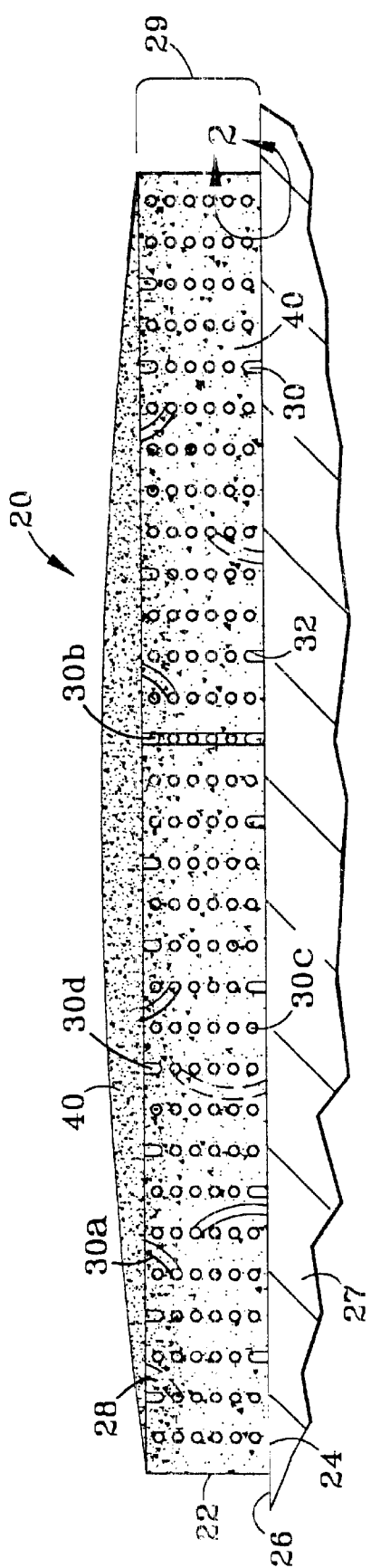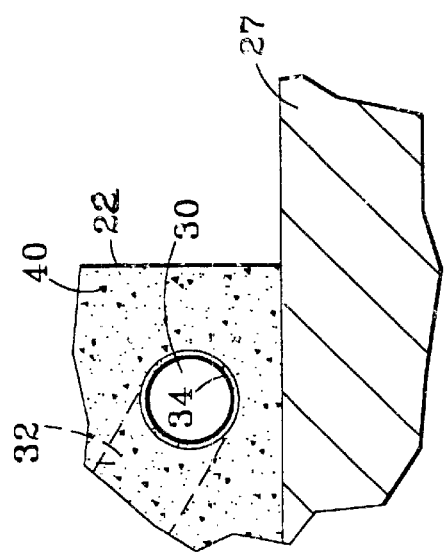
FIG. 1a
FIG. 2

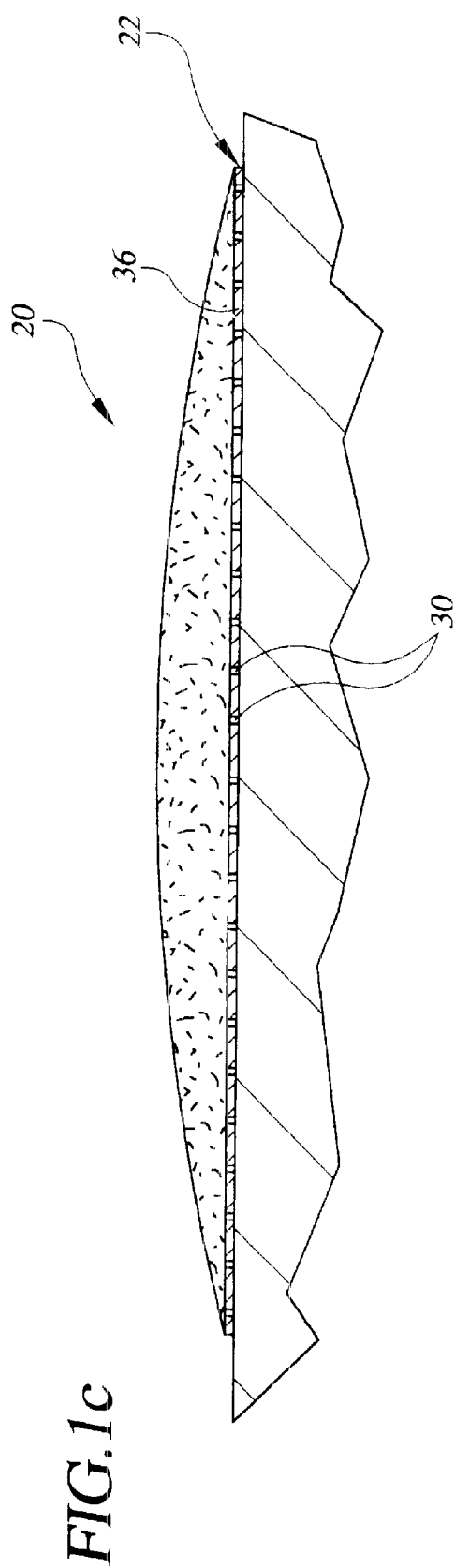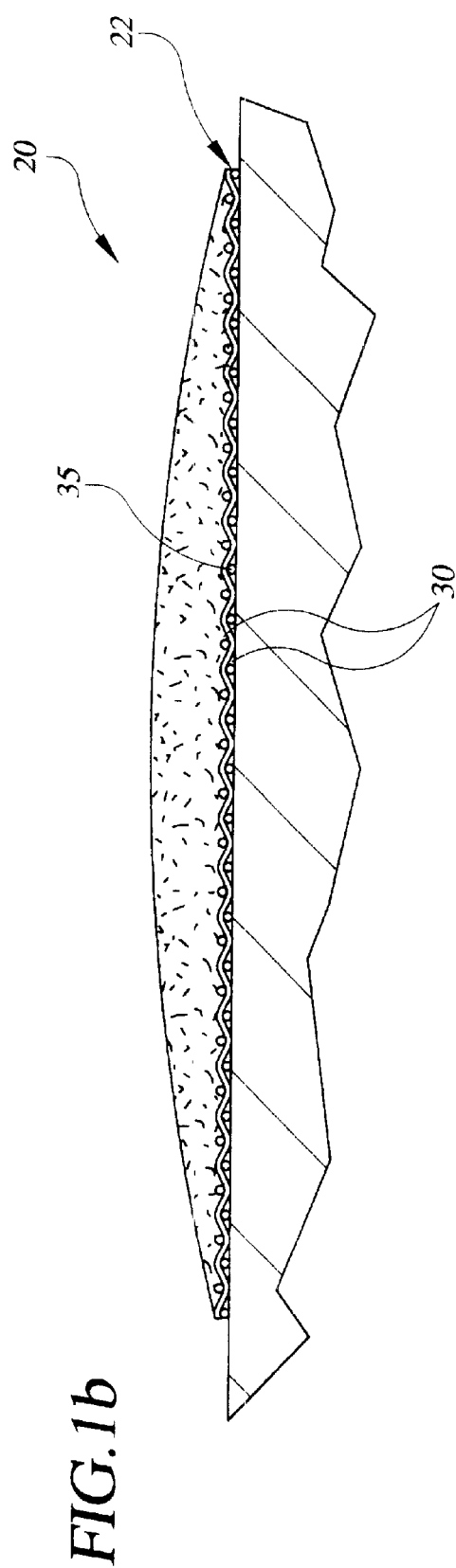
FIG.1c
FIG.1b

ELECTROLYTIC DEVICE

FIELD OF THE INVENTION

The present invention relates generally to an electrolytic antiseptic device and, in particular, to an electrolytic therapeutic device comprising a silver-bearing material and at least one metal other than silver, e.g., zinc. The invention also pertains to an antiseptic and therapeutic method of treating tissue through the use of a silver-bearing material and a metal other than silver.

BACKGROUND OF THE INVENTION

The art of applying a low voltage electric current to control microbes and promote healing action for medical and hygienic purposes has been developing for many years. In particular, it is known that the use of a low voltage electric field applied through a reservoir can be used to deliver drugs or agents in the reservoir systematically or to produce a localized therapeutic effect. Moreover, the application of electricity to the body, with or without drugs or agents, can be used therapeutically. Direct current fields can exert a microbicidal effect, and electric voltage can also via electrophoresis induce agents or medications to penetrate tissue more deeply, and can induce the agents to penetrate structures on implants such as biofilms. Further therapeutic effects of electricity include control of pain, edema and acceleration of wound healing. Moreover, the localized effect of drugs and agents can be greater at the delivery site than the effect that is seen with topically or systematically delivered agents alone, due to higher available concentrations at the site, over time.

Such low voltage antibacterial devices are able to infuse charged molecules, i.e., iontophoresis, as well as uncharged molecules into the body, i.e., electro-osmosis. For example, U.S. Pat. No. 5,298,017 to Theeuwes et al. ("the '017 patent), which is incorporated herein by reference, describes a iontophoretic process by which drugs are delivered transdermally or transmucosally under the influence of an electrical potential. Iontophoretic devices use two distinct electrodes, with at least one of the electrodes being applied to the body. These devices typically utilize a conventional electric power source, such as a battery, to develop the electric current. In some cases, the power source is located separately from the device and in some cases the power source is integrated into the device. These devices also rely solely on the creation of a discrete ion pathway incorporating the body or tissue to effect an electromotive force via forms defined by the sequence of a first electrode, tissue and a second electrode.

There are devices described in the prior art that rely on the electric field generated by the device itself. The power source generally provides no therapeutic value itself other than to provide the electric current necessary to drive the iontophoretic or electro-osmotic device to deliver an agent that is different from the electrode metals. Further, if the power supply should fail for any reason, the device is typically rendered useless. Also, where the power source located away from the device, limitations are imposed on patient mobility. Still further, even when the prior art integrates the conventional power source into the device there are limitations. In particular, the prior art makes it clear that the conventional power source must be protected from short circuiting itself. Consequently, great lengths have been taken to insure that the two electrodes are insulated in order to limit the possibility of a short circuit. Further limitations of these devices include high cost due to wires, electrical insulation, battery failure, problems with user compliance, maintenance, and damage.

In spite of the fact that the use of external power sources is prevalent in the art of iontophoresis and electro-osmosis, it is known to rely exclusively on the electric potential generated by the galvanic couple between dissimilar materials, e.g., a zinc electrode and a silver/silver chloride counter electrode, to deliver a drug. For example, the embodiment of the device illustrated in FIG. 2 of the '017 patent does not use an external power source. While the primary purpose of such devices is to deliver a drug present in a drug reservoir, as a consequence of the galvanic couple ions of the material used for the anode and/or cathode are delivered into the body. Unfortunately, because the anode and cathodes of such prior art devices are typically made from materials having a relatively low total surface area, the rate of metallic ion transfer from the metallic electrodes is typically lower than desired for satisfactory therapeutic effects.

As described in U.S. Pat. No. 5,814,094 to Becker et al. ("the '094 patent"), iontophoretic devices that provide silver ions for wound healing are known. Use of silver-coated nylon as the anode for the iontophoretic device of the device of the '094 patent provides a relatively high total surface area material as the source of silver ions. However, the device of the '094 patent features the use of an external power source connected to the silver-coated nylon anode to generate the electrical potential that drives the silver ions into the body, and so suffers from the limitations of other iontophoretic devices described above. In view of the foregoing, there is an apparent need for low cost, simple, robust, flexible, user compliant electrolytic apparatus that offers the benefits of the prior art and offers additional uses.

SUMMARY OF THE INVENTION

One aspect of the present invention is an electrolytic device that comprises a structure having a first surface with a first surface area, a thickness region and a plurality of openings in the thickness region. The plurality of openings is defined by a plurality of inner surfaces that together have an inner surface area, with the plurality of inner surfaces comprising silver. The device also includes a metal-bearing material other than silver that is interspersed throughout at least some of the plurality of openings.

Another aspect of the present invention is an electrolytic device that comprises a structure having a first surface with a first surface area, a thickness region and a plurality of openings in the thickness region. The plurality of openings is defined by a plurality of inner surfaces that together have an inner surface area, with the first surface and the plurality of inner surfaces comprising silver. The device also includes a metal-bearing material other than silver that contacts the first surface.

Still another aspect of the present invention is an electrolytic device that comprises a first region having a structure having a first surface with a first surface area, a thickness region and a plurality of openings in the thickness region. The plurality of openings is defined by a plurality of inner surfaces that together have an inner surface area, with the plurality of inner surfaces comprising silver. The device also includes a second region comprising a metal-bearing material other than silver. The second region does not touch the first region.

Yet another aspect of the present invention is a method of administering silver and a metal other than silver to a body.

The first step of the method involves providing a porous silver-bearing structure and a metal-bearing material other than silver proximate said structure. Next, the porous silver-bearing structure and the metal-bearing material other than silver is applied to the body so that at least the structure contacts the body and so that no voltage source is connected to the structure and the metal-bearing material. Finally, before or after the preceding step, moisture is added to the structure and the metal-bearing material other than silver.

BRIEF DESCRIPTION OF THE DRAWINGS

FIGS. 1a–1f are each a cross-sectional view of one embodiment of the electrolytic device of the present invention;

FIG. 2 is an expanded view of a small portion of the silver bearing layer of the device of FIG. 1a illustrating the porous structure of the silver bearing layer;

DETAILED DESCRIPTION OF THE INVENTION

Figure 1E:
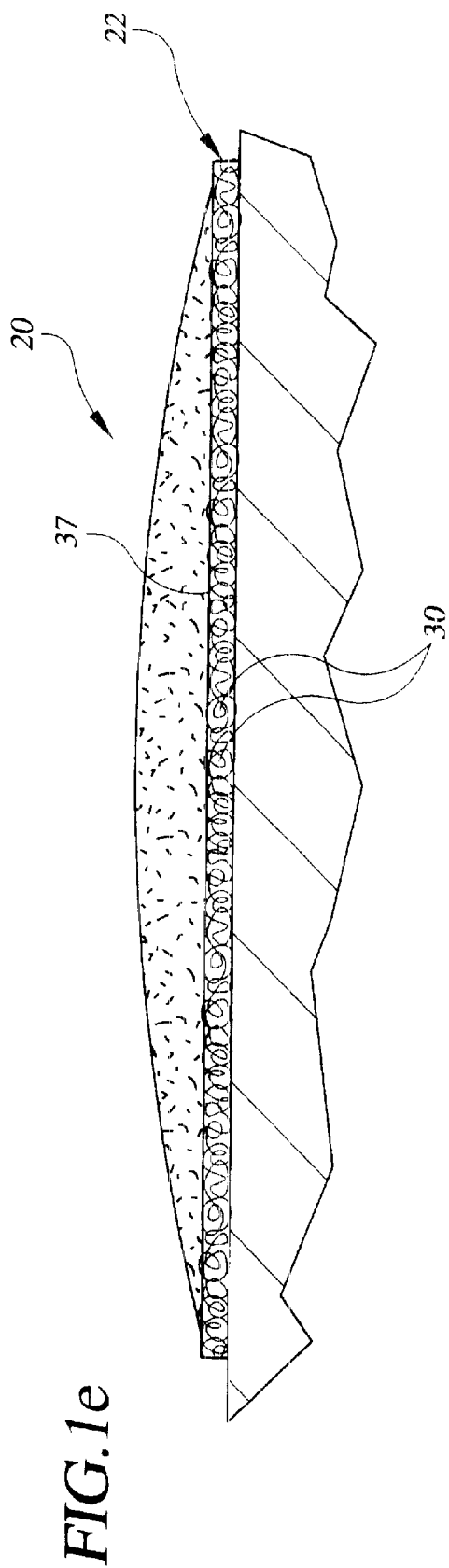
Figure 1D:
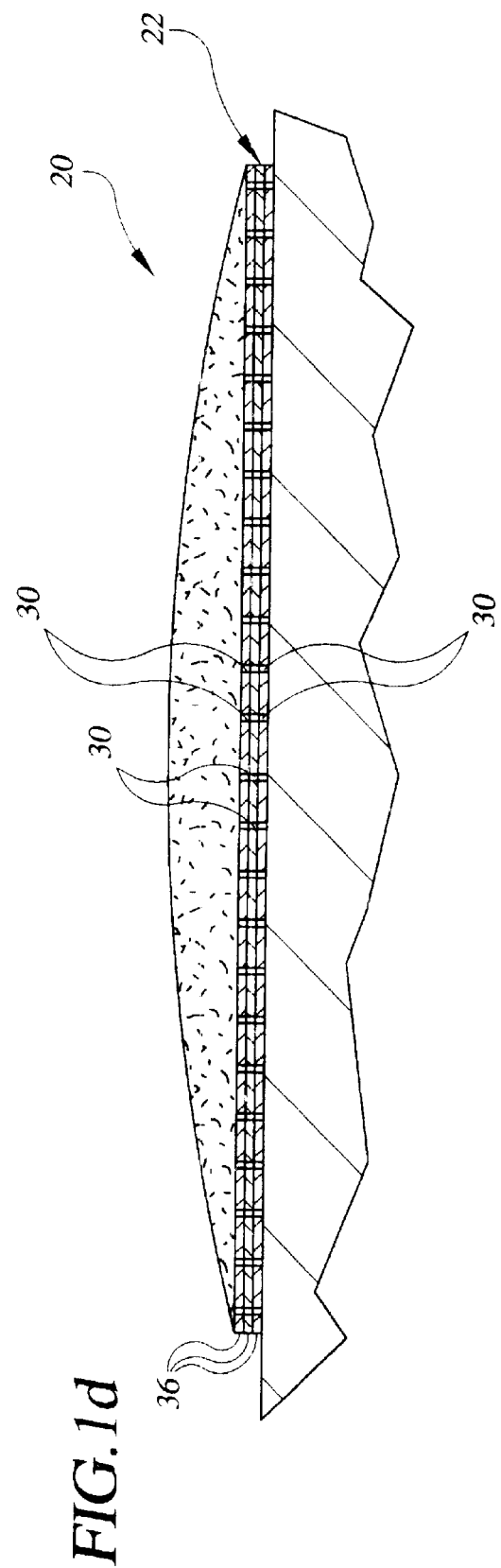
Figure 1F:
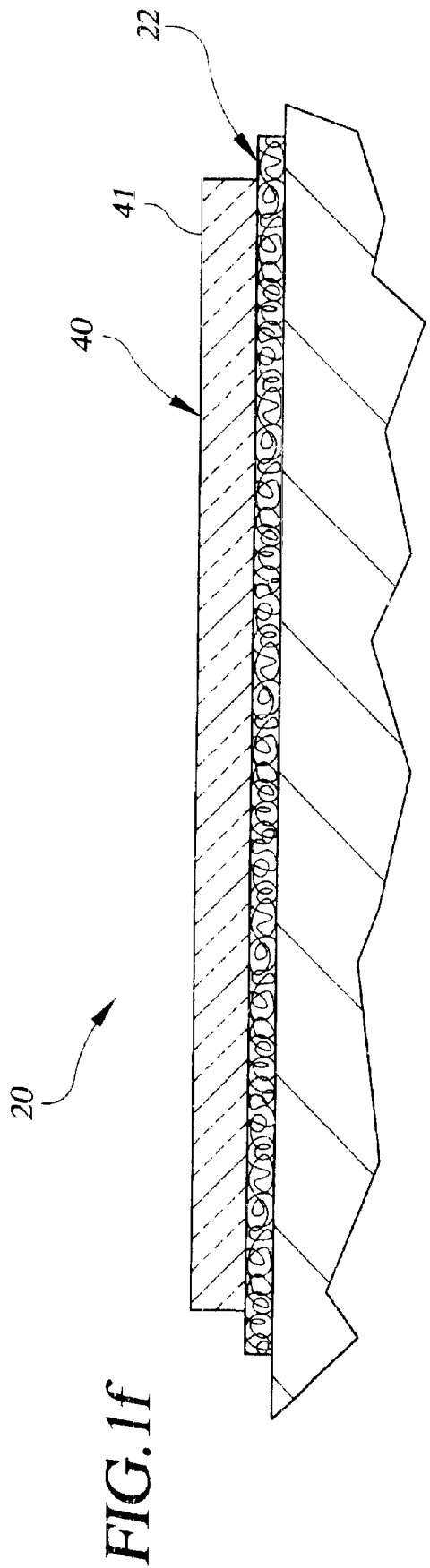

Referring to FIG. 1, and particularly to FIG. 1a, electrolytic healing device 20 of the present invention includes, in one embodiment, a porous base layer 22 having a body-contacting surface 24 designed to contact a surface 26 of a body 27 and an opposite surface 28. (References made below to FIG. 1 without an "a" through "f" sub-identifier refer to FIG. 1a and any of FIGS. 1b–1f that may be relevant to the context of the reference.) Surface 26 may be the top surface of skin, the wall of an intra-body cavity, e.g., the vagina, the space between a cheek and gum, or the wall of a deep wound.

Turning next to FIGS. 1 and 2, base layer 22 is made from a liquid permeable, high total surface area material. In this regard, base layer 22 has within its thickness 29 a plurality of openings 30 that are defined by a plurality of surfaces 32.

The majority, if not all, of surfaces 32 that will be contacted by liquid, when liquid is present within base layer 22, preferably comprise silver layer 34 (FIG. 2). However, in some cases, e.g., where a lower silver ion concentration is desired, or when it is desired to reduce the cost of manufacturing base layer 22, it may be desirable to provide silver on only a limited percentage of the surfaces 32 within the base layer. Silver layer 34 may cover surfaces 32 or may be integrated into the surfaces. The thickness of silver layer 34 may vary, but preferably ranges from 0.2 to 6 microns. In addition, while silver layer 34 is preferably made from silver that is at least 99.99% to 99.9999% pure, silver alloys such as sterling silver, silver salts and the like may also be used. Preferably, the surface area of silver layer 34 on all surfaces 32 within thickness 29 plus the surface area of surface 24, referred to herein as the "total surface area" of base layer 22, is equal to at least 1.1 times the surface area of surface 24. For the purposes of the present invention, high total surface areas are preferable. Thus, a total surface area of 2 or even higher is desirable.

Various materials may be used as base layer 22. Silver-coated nylon is an ideal material for base layer 22 as it has a relatively high total surface area, i.e. greater than 1.1 Silver-coated fabrics made from materials other than nylon may also be used, e.g., polypropylene, polyimid and polyethylene. FIG. 1b shows device 20 having base layer 22 made of a silver-coated fabric 35 having openings 30 defined therein by the spaces between adjacent fibers of the fabric Also, base layer 22 may be made from one or more sheets of silver-coated screen, one or more sheets of silver foil having a plurality of holes or slits formed therein, silver-coated fibers that are spun, compressed or otherwise aggregated to form a layer of material and form a sponge-like material comprising silver. FIGS. 1c and 1d show, respectively, base layer 22 of device 20 as comprising a single foil sheet 36 and a plurality of foil sheets 36, wherein each foil sheet in both figures has a plurality of openings formed therein. FIG. 1e shows base layer 22 of device 20 as comprising a sheet 37 of aggregated silver-coated fibers that define a plurality of openings 30 thereamong. In addition, base layer 22 may be made from sheets of polymeric material such as TEFLON®, polypropylene, and polyethylene, with at least the body-contacting surface 24 being coated with silver and with a plurality of openings formed therein on which silver layer 34 is provided. Other high total surface area materials are also encompassed by the present invention, i.e., materials having a total surface area in excess of 1.1 times the area of body-contacting surface 24. A suitable process for applying silver to whichever substrate is chosen is described in U.S. Pat. No. 4,241,105, which is incorporated herein by reference. Also, it is desirable, but not essential, that base layer 22 be constructed of a flexible material so that it may conform to an irregular surface 26 of body 27.

In view of the different materials that may be used for base layer 22, it is apparent that openings 30 will have different configurations. Thus, openings 30 may have a circuitous path, as indicated by opening 30a, may extend vertically entirely through base layer 22, as indicated by openings 30b, may extend horizontally, as indicated by openings 30c, or may extend only partially through the base layer, as indicated by openings 30d. Openings 30 may have a regular configuration, as illustrated in FIG. 1, or an irregular configuration. Thus, the relative size and configuration of openings 30 is a schematic, not an absolute, depiction of the openings. In any event, openings 30 provide a pathway, either direct or circuitous, from opposite surface 28, through thickness 29, to body-contacting surface 24.

Electrolytic healing device 20 also includes a metal 40, which is a metal other than silver, that contacts base layer 22. The term "metal 40," as well as the terms "metal 140,"

"metal 240," "metal 340" and "metal 440" referred to below, are used broadly herein so as to include metals, metal oxides, metal salts and other metal-bearing materials. Metal 40 is preferably zinc oxide, but aluminum, cobalt, copper, gold, iron, magnesium, platinum, titanium and elemental zinc may also be used. In addition, metal 40 may comprise compounds providing free dissolution of metal ions, such as zinc gluconate, zinc acetate, zinc chloride, zinc citrate, zinc propionate, zinc sulphate heptahydrate, zinc butyrate, zinc formate, zinc glycolate, zinc glycerate, zinc lactate, zinc sulfate, ferrous oxide, ferrous sulphate, and titanium oxide. Other zinc salts which are soluble in water and have low pK values, which indicate a high rate of zinc ion release, may also be used. Other metal salts and compounds that release metal ions upon exposure to an aqueous medium may also be used. Furthermore, metal 40 may be made from a material that physically dissociates when exposed to moisture, e.g., a compressed powder with a water-soluble binder. FIG. 1e shows metal 40 of device 20 as being a dissociatable compressed powder in the form of a tablet 41, which, as shown, may directly contact the upper surface of base layer 22. Metal 40 is preferably provided as a powder having a mean particle size ranging from 0.5 to 400:m. Alternatively, metal 40 may be provided in a matrix, e.g., as zinc oxide cream, as fibers, shreds, filaments, granules, or as pastes and plasters.

In any event, it is preferred that metal 40 be provided in a form that will allow it to penetrate into openings 30 so as to be interspersed within at least a portion of thickness 29 of base layer 22, preferably including at body-contacting layer 24. Or considered alternatively, openings 30 should be sized so as to allow metal 40 to penetrate and become interspersed within the openings. As described in more detail below, when device 20 is hydrated with moisture, metal 40 reacts with silver layer 34 to create a galvanic electric potential that dissociates silver ions and ions of metal 40 from the device for delivery into tissue of body 27 that device 20 contacts.

Figure 3:
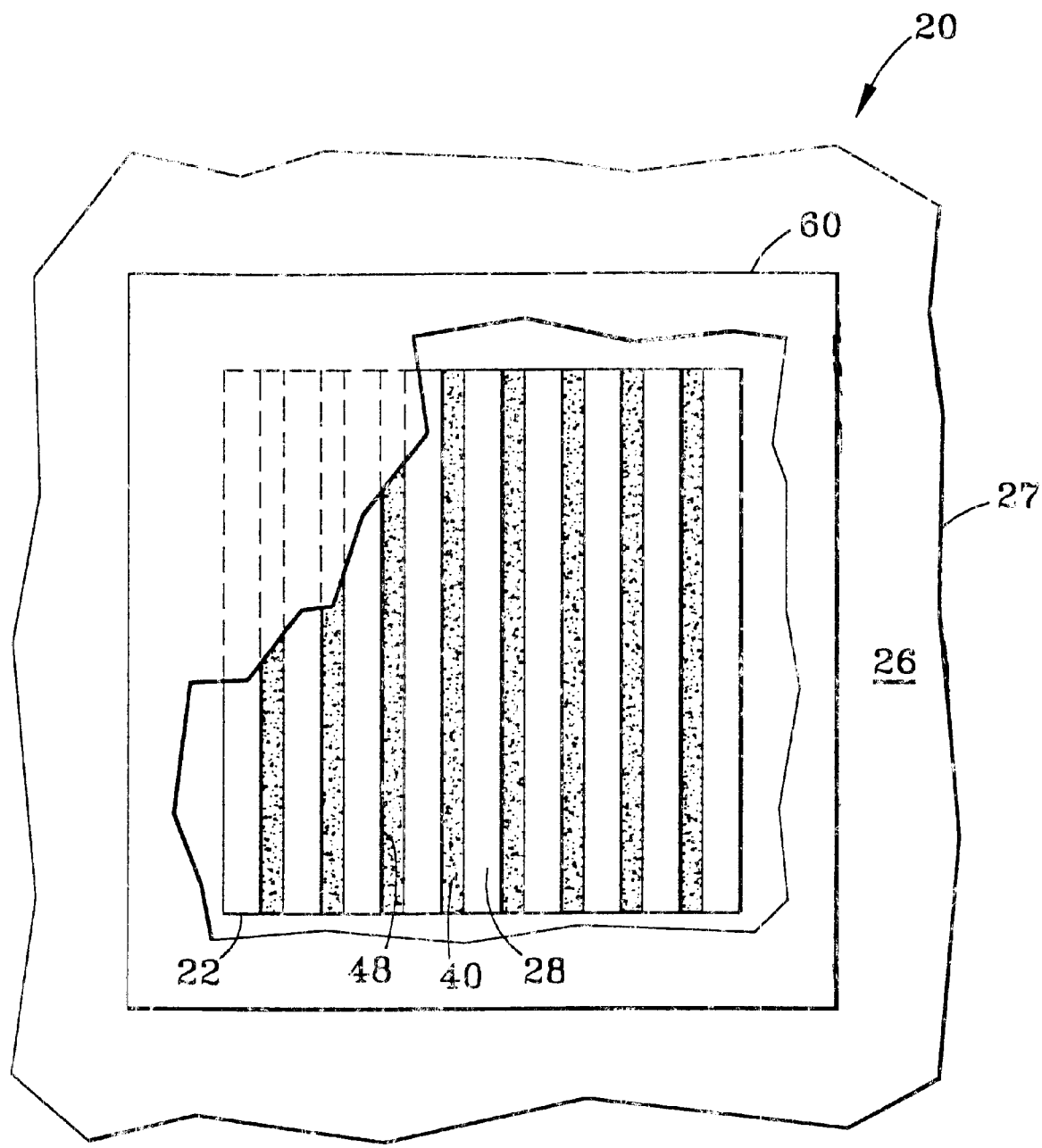
FIG. 3 is a top view of an embodiment of the present invention having a plurality of recesses.

By virtue of the plurality of openings 30 in base layer 22, metal 40, particularly when in powder form, tends to be retained within the base layer. However, in some cases it may be desirable to provide a plurality of recesses 48 in opposite surface 28 for retaining metal 40, as illustrated in FIG. 3. Recesses 48 may have an elongate, substantially straight configuration, as shown, or may have a curved, discontinuous or other configuration.

Figure 4:
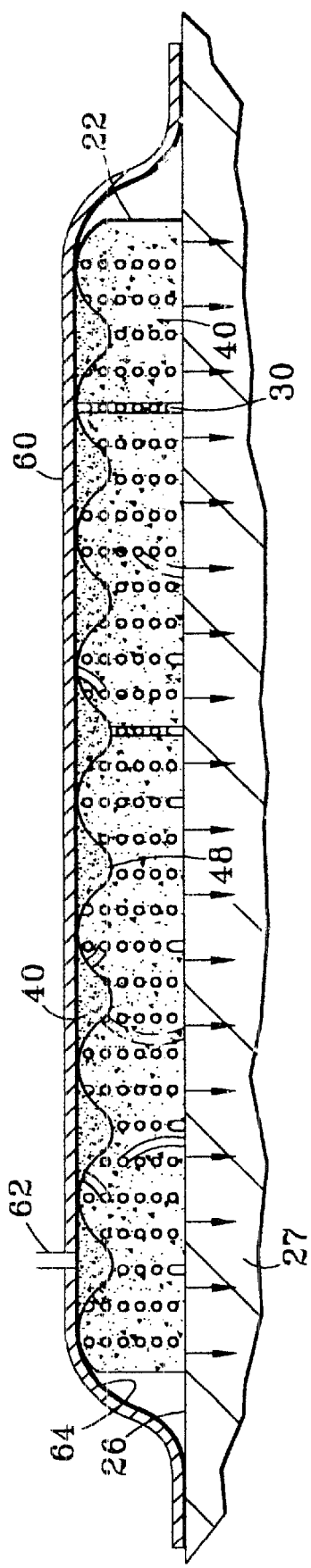
FIG. 4 is a cross-sectional view of the device of FIG. 1a, with a barrier layer covering the device.

Turning next to FIGS. 1, 3 and 4, in some cases device 20 is applied directly to surface 26 of body 27, e.g., without the use of a cover layer or adhesive strips or the like, in the form illustrated in FIG. 1. However, in many cases it is desirable to provide a barrier layer 60 (FIGS. 3 and 4) covering metal 40 and base layer 20. Preferably barrier layer 60 is sized to extend beyond the outer margins of device 20, as illustrated in FIGS. 3 and 4, so that it contacts surface 26 of body 27. Barrier layer 60 may be secured with a suitable adhesive 64 applied to the inner surface of the barrier layer, with adhesive strips (not shown) or by other means. Barrier layer 60 is preferably liquid impervious, although may be constructed of materials that permit the transfer of water vapor. Suitable materials for barrier layer 60 are sheets of hydrophobic material that include, but are not limited to, polyisobutylenes, polyethylene, polyisoprenes and polyalkenes, rubbers, copolymers such as KRATON®, polyvinylacetate, ethylene vinyl acetate copolymers, polyamides such as nylons, polyurethanes, polyvinylchloride, acrylic or methacrylic resins such as polymers or esters of acrylic or methacrylic acid with alcohols such as n-butanol, 1-methyl pentanol, 2-methyl pentanol, 3-methyl pentanol, 2-ethyl butanol, isooctanol, n-decanol, alone or copolymerized with ethylenically unsaturated monomers such as acrylic acid, emthacrylic acid, acrylamide, methancrylamide, N-alkoxymethyl acrylamides, N-alkoxymethyl methacrylamides, N-tert-butylacrylamide, itaconic acid, N-branched alkyl maleamic acids wherein the alkyl group has 10–24 carbon atoms, glycol diacrylates, and blends thereof. Most of the above-mentioned hydrphobic polymers are heat fusible. Other suitable materials are described in U.S. Pat. No. 5,298,017 to Theeuwes et al. Preferably, although not necessarily, barrier layer 60 includes a port 62 through which moisture may be introduced to the region enclosed by the barrier layer, i.e., into metal 40 and base layer 22. If desired, a valve (not shown) and/or tube (not shown) may be coupled with port 62.

Figure 5:
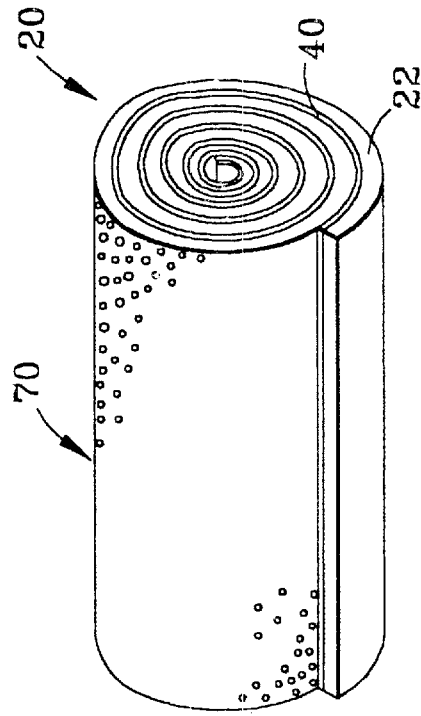
FIG. 5 is a perspective view of any one of the embodiments illustrated in FIGS. 1a–1f rolled about its central axis so as to form a multilayer cylinder.

Referring now to FIGS. 1 and 5, device 20 may have a wide range of substantially planar configurations, including a rectangular, circular and other irregular geometric configuration. Also, device 20 may be rolled up around a central axis to form a multi-layer cylinder 70, as illustrated in FIG. 5. In addition, device 20 may be a thread-like structure such as floss or suture (neither shown) made from a single filament or a plurality of fibers woven or otherwise combined to form the thread-like structure. Other configurations for device 20 are also encompassed by the present invention.

Figure 6:
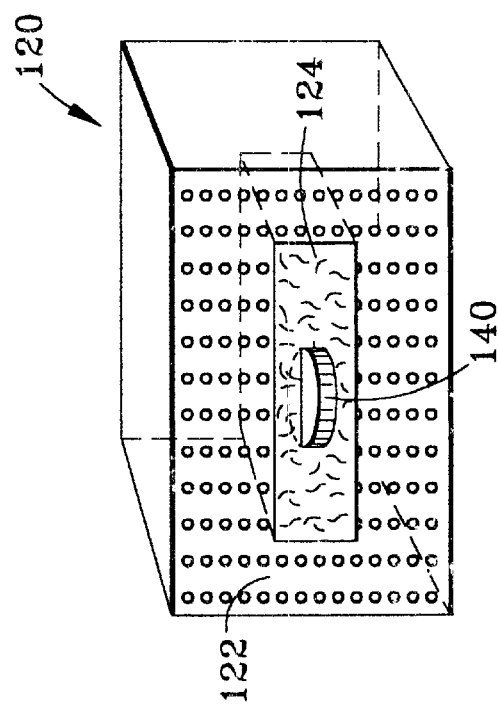
FIG. 6 is a perspective view of a cross section of an embodiment of the present invention where the metal other than silver is separated from the silver bearing layer.

Turning next to FIG. 6, another embodiment of the present invention is an electrolytic device 120 having an outer layer 122 made from a porous silver-bearing material. Outer layer 122 may be made from the same materials as base layer 22, as described above. However, it is not essential that outer layer 122 be made from a high total surface area material unless a compact arrangement is desired. In this regard, outer layer 122 may be made from porous sheet material, such as porous foil, screen, meshes, and other sheets of porous polymeric material and aggregates or matrices of metal-bearing material.

Device 120 also includes absorbent material 124 that is at least partially, and preferably totally, surrounded by outer layer 122. Absorbent material 124 may be made from cotton, rayon, polyimids and other absorbent materials. Disposed within absorbent material 124 is a metal 140 other than silver. Metal 140 is preferably totally surrounded by absorbent material 124, but in some cases it may be desirable to only partially surround the metal with the absorbent layer. Again, metal 140 preferably is preferably zinc oxide, but aluminum, cobalt, copper, gold, iron, magnesium, platinum and elemental zinc oxide and the like may also be used. Absorbent material 124 is sized or otherwise constructed so that metal 140 does not contact outer layer 122.

Metal 140 is preferably, but not necessarily, provided in a state whereby it will physically dissociate when exposed to moisture. Metal 140 may be formed as a structure of varying configurations, e.g., tablet, cylinder or cube, and may be made from pressed powder or other structures, or may be loose powder, granules, nuggets, strips and structures of other configuration. Other metal-bearing materials of the type disclosed in U.S. Pat. No. 5,208,031 to Kelley and U.S. Pat. No. 4,762,715 to Lukas may also be used.

Figure 7:
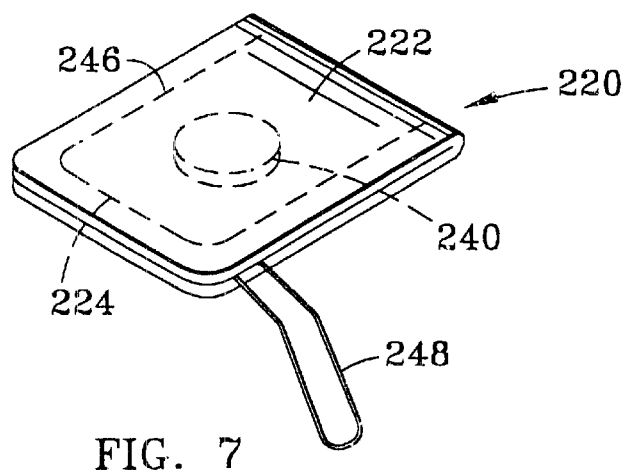
FIG. 7 is a perspective view of an embodiment of the present invention where the metal other than silver is surrounded by and in contact with the silver bearing material.

Referring next to FIG. 7, yet another embodiment of the present invention is a device 220 having an outer layer 222 made from a porous silver-bearing material. Outer layer 222 may be made from the same materials as base layer 22, as described above. However, as with outer layer 122, it is not essential that outer layer 222 be made from a high total surface area material. In this regard, outer layer 222 may be made from porous sheet material, such as porous foil, sheets of porous polymeric material and other materials used for the electrodes in U.S. Pat. No. 5,298,017.

Outer layer 222 is formed so as to include an interior cavity 224 in which a metal 240 other than silver is encapsulated. Device 220 may have various configurations. However, in a preferred configuration outer layer 222 is a flexible sheet of material that is folded over itself and then stitched along line 246 so as to form interior cavity 224 in which metal 240 is disposed. Optionally, a retrieval cord 248 may be attached to device 220 to facilitate removal of the device from the region of body 27 in which it is positioned. Alternatively, device 220 may have an elongate configuration with an integral "tail" that may be used to retrieve the device from the body cavity where it is inserted.

Figure 8:
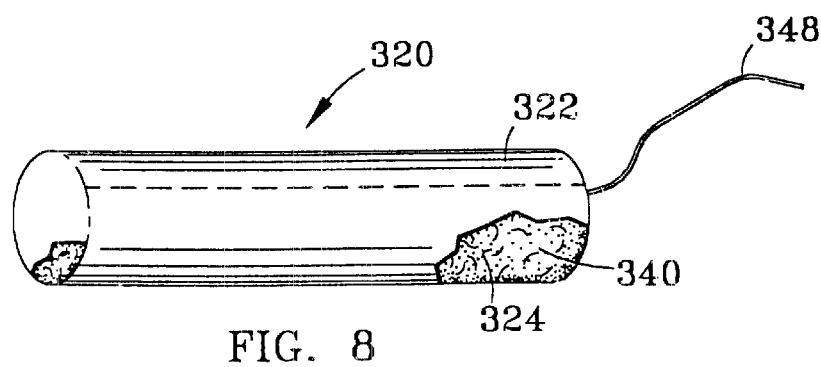
FIG. 8 is a perspective view of an embodiment of the present invention where the metal other than silver is dispersed within an absorbent material that is covered by a layer of silver bearing material.

Turning now to FIG. 8, yet another embodiment of the present invention is device 320. The latter is similar to device 120 in that it includes outer layer 322 that is identical to outer layer 122, and it includes absorbent material 324 that is identical to absorbent material 124. Device 320 differs from device 120 in that it includes metal 340 which is distributed throughout at least a portion of the absorbent material, and at least some of metal 340 contacts outer layer 322. Metal 340 is preferably provided in powder or other particulate form, although it may also be provided in fiber, wire or other configuration. Device 320 may have a variety of configurations, one of which is the tampon configuration illustrated in FIG. 8. When configured as a tampon or other structure to be inserted into a body cavity, it is desirable to attach a retrieval cord 348 to device 320. Alternatively, device 320 may have an elongate configuration with an integral "tail" that may be used to retrieve the device from the body cavity where it is inserted.

Figure 9:
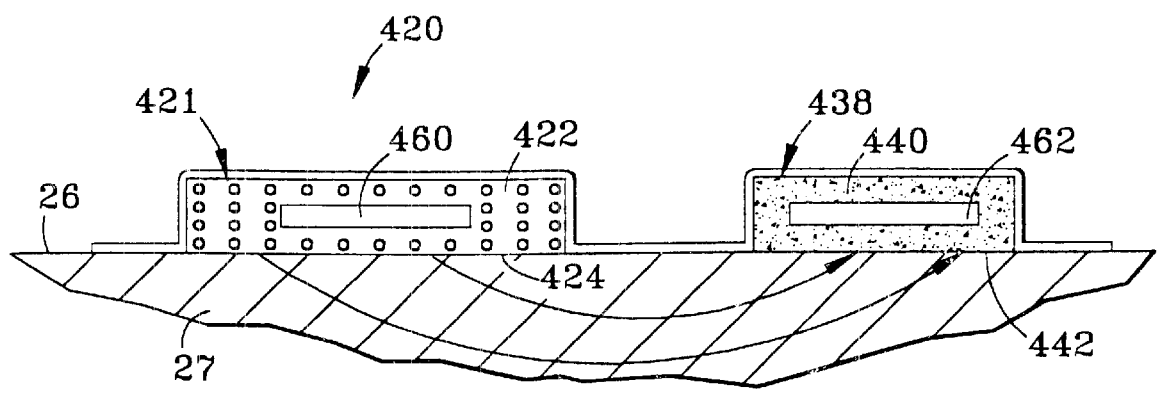
FIG. 9 is a cross-sectional view of an embodiment of the present invention having a first region with a silver bearing material, a second region having a metal other than silver and separated from the first region, and a drug reservoir in at least one of the first and second regions.

Referring next to FIG. 9, still another embodiment of the present invention is device 420. The latter includes a first region 421 in which a high total surface area silver-bearing material 422 is disposed. Material 422 may comprise any of the materials used for base layer 22, as described above. First region 421 is constructed so that material 422 includes a body-contacting surface 424, whereby material 422 directly contacts surface 26 of body 27. Device 420 also includes a second region 438 in which metal 440 is disposed. Metal 440 may comprise any of the materials used as metal 40 or 140, as described above. Second region 438 is constructed so that metal 440 includes a body-contacting surface 442, whereby metal 440 directly contacts surface 26 of body 27.

Device 420 includes a housing 450 for supporting and containing material 422 in first region 421 and metal 440 in second region 438. Housing 450 is constructed so that first region 421 is positioned proximate to, but is spaced from, second region 438. Also, housing 450 may be constructed to function as a barrier layer that blocks the passage of fluid, although may optionally permit the passage of moisture or water vapor. Use of semi-permeable membranes for housing 450, also referred to as porous occlusive films, permit the region enclosed by the housing to "breathe," yet provide suitable microbial and liquid occlusion. Materials suitable for barrier layer 60, as described above, may also be used for housing 450. Optionally, housing 450 may include openings (not shown) above first region 421 and second region 438 via which, among other things, moisture may be added to the regions.

Device 420 may be constructed so that first region 421 includes a drug reservoir 460 and second region 438 includes a drug reservoir 462. If desired, only one of first region 421 and second region 438 includes, respectively, drug reservoirs 460 and 462. Drug reservoirs 460 and 462 are designed to contain drugs other than silver and metal 440, respectively. In this regard, a wide range of drugs and agents may be contained in reservoirs 460 and 462, including the range of drugs and agents described in U.S. Pat. No. 5,298,017. However, it is generally preferred that if polar, i.e., charged, drugs are used, positively charged drugs are provided in reservoir 460 and negatively charged drugs are provided in reservoir 462.

Figure 10:
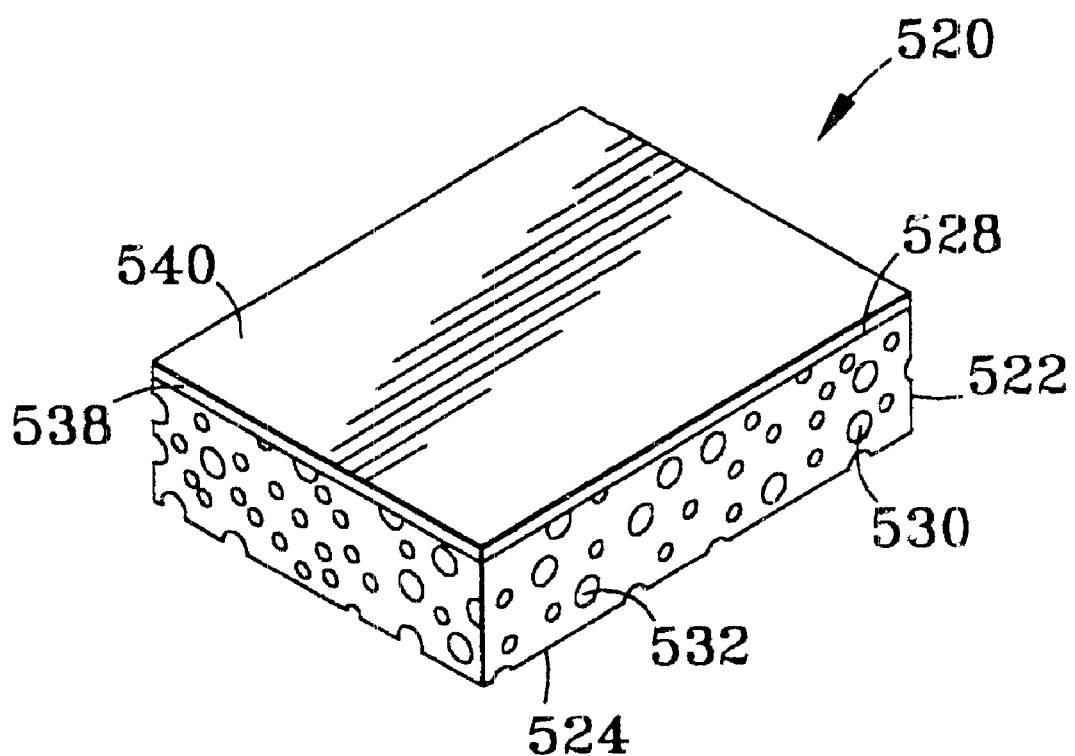
FIG. 10 is a perspective view of the sponge embodiment of the present invention.

Still another embodiment of the present invention is device 520, as illustrated in FIG. 10. Device 520 includes a first layer 522 made from a sponge material such as hydrophilic loams, cellulose, gauze, cotton. polyimids, sponge rubber and natural sponge. First layer 522 includes bottom surface 524 and a top surface 528. A plurality of openings 530 defined by inner surfaces 532 are provided in first layer 522. At least inner surfaces 532, and preferably bottom surface 524, comprise silver coated on, or integrated with, the inner surfaces and bottom surface.

Device 520 also includes a second layer 538 made from an abrasive material such as copper or steel wool, or conventional abrasive layers used on kitchen sponges of the type identified by the mark SCOTTY®. Second layer 538 contains metal 540, which is a metal other than silver. Preferably, metal 540 is copper, although other suitable materials include aluminum, gold, iron, magnesium, platinum and zinc. Metal 540 may be provided in the forms described above for metal 40, but may also be provided in sheet form. Metal 540 may be distributed throughout the interior of first layer 522. Also, metal layer 540 may also be embedded as a discrete structure or structures at various locations within first layer 522. Second layer 538 is adhered to top surface 528 of first layer 522.

Still another embodiment of the present invention, not illustrated in the Figures, is a composition comprising pieces of silver and pieces of metal 40 interspersed within a viscous matrix such as hydrogenated coconut oil, hemp seed oil, olive oil, beeswax, candella wax, petroleum jelly. The composition may be used in a variety of applications, including as lipstick, lip balm, sunscreen or other plasters or salves. The silver is preferably in fine chopped strand form, and may be provided as fibers, slivers, granules, powder and/or other particulate form. It is preferred that the materials used for base layer 22, described above, be subjected to suitable mechanical, chemical or other treatment so as to create particulates having the configuration described above. However, in some cases it may be desirable to use silver powder. Metal 40 is provided in one or more of the various forms used in device 20 as described above. Furthermore, metal 40 may comprise any of the metals used in device 20, as described above.

Discussing now the operation of device 20 illustrated in FIGS. 1–4, the treatment of a large variety of pathologies may be encouraged through the use of the device, including without limitation, cuts, incisions (including surgical incisions), abrasions, lacerations, fractures, contusions, burns, amputations and edema. The device may be used hold and to deliver drugs or agents other than those created by the electrode metals to affect systemic dosages to the body. Also, device 20 may be used for tissue replacement, where the cells of some body tissues produce more cells of their own kind to replace missing portions. Further, device 20 may be used for tissue regeneration, where portions of, or even entire, limbs, internal organs and other portions of the body are regrown. In addition, silver ions provided by device 20 in the manner discussed below have significant antibacterial and antifungal effects. In this regard, silver is a well-known antibiotic. In addition, silver has demonstrated antiviral effects. Furthermore, ions from metal 40, which are provided in the manner discussed below, provide, in the case of zinc, therapeutic benefits including but not limited to, control of viruses and autolytic debridement of wounds and scar tissue. Zinc is necessary for a wide variety of metabolic processes, including the synthesis as well as the degradation of nucleic acids, proteins, carbohydrates, and lipids. The high prevalence of zinc in mammal tissue speaks to its importance and role as a nutrient. Likewise trace minerals from metals such as copper also affect tissue function.

Prior to use of device 20, it will often be desirable to activate the device by adding a suitable liquid such as water, saline solution and solution or lactated saline solution (Ringer's Solution). In some cases, it may be desirable to provide metal 40 via the liquid that is used to activate the device. The activating liquid can also comprise drugs or agents for therapeutic effects or to retain moisture such as sugar, or to provide nutrition directly to tissue, such as fetal calf serum. When device 20 is intended for use in a moist environment, i.e., where substantial blood, saliva, sweat or other liquid is present, application of liquid prior to bringing the device into contact with the body may not be necessary. When device 20 includes a port 62, liquid may be added after application. Also, when barrier layer 60 is used, liquid may be added after base layer 22 and metal 40 are brought into contact with body 27, but before barrier layer 60 is applied.

Device 20 is applied to body 27 so that its body-contacting surface 24 contacts surface 26 of the body. Once activated by the addition of liquid, surfaces 32 coated with silver 34 begins generating silver ions. These ions travel into body 27 by virtue of a galvanic electric potential created between base layer 22, which functions as one electrode, and metal 40, which functions as the other electrode, and the electrolysis resulting from the potential. Because the base layer 22 and metal 40 are allowed to touch, the galvanic electrical potential results in active dispersion of electrode metal front both the base layer and the metal, causing a high concentration of free metal ions to be maintained in the liquid added to device 20. A useful galvanic coupling of the short-circuited electrodes (i.e., base layer 22 and metal 40) also occurs with body 27 that provides ion migration transport via surface 26 into the body. The high concentration of ions about device 20 enables osmosis, or oligodynamic transport, to carry metal ions into the body.

By providing base layer 22 with a total surface area, as defined above, that is more than 1.1 times the area of body-contacting surface 24, a much higher concentration of silver ions is provided than with devices featuring a body-contacting silver electrode made from silver foil or other monolithic material not including openings within the thickness of the material on which the silver is provided. In this regard, after device 20 has been activated for a sufficient time that generation of silver ions is at a maximum, it is believed that liquid taken from the device will show silver ion concentrations of 90 to 1000 parts per million. While known electrolytic healing devices featuring an external power source may generate a higher silver concentration than device 20, they do so with the disadvantages associated with such power sources, as discussed above.

Ions from metal 40, e.g., zinc ions, are also generated when device 20 is activated by the addition of moisture. These ions are generated by the galvanic electric potential generated between metal 40 and base layer 22. It is thought that liquid from device 20, when metal 40 is zinc oxide, will contain zinc ions at concentrations of 10 to 500 parts per million.

When device 20 is rolled up to form a multi-layer cylinder of the type illustrated in FIG. 5, the operation of such device proceeds substantially as described above. It is the environment in body 27 that the multi-layer cylinder is intended to be inserted that differentiates it from the single-layer versions of the invention illustrated in FIGS. 1–4. In this regard, the multi-layer cylinder version of device 20 is adapted for insertion in body cavities such as a nostril, the vagina and ear, deep wound, fistula, or between body structures such as the gum and the inner wall of the cheek.

Operation of device 120 illustrated in FIG. 6 differs from all other embodiments of the invention, except device 520, in that the silver-bearing material in outer layer 122 is separated from metal 140 by absorbent material 124. After activation of device 120 by the addition of liquid, electrolytic interaction of the metal 140 causes a high rate of positive ionic release from the outer layer 122 that 1) increases the cidal effect by raising the concentration of silver ions in the contacting solution, 2) acts as a cleaning catalyst getting organic material to leave the surface or breaking chemical bond, 3) delivers weak DC fields to microbes killing them, and 4) leaves metal ions on surfaces for residual inhibition of microbes, and odors. Device 120 functions by interaction of metal 140 with outer layer 122 by galvanic coupling upon wetting of the whole device. Electrolytic dispersion of silver ions from 122 occurs into the liquid present in both in layer 122 and absorbent material 124. Although the voltage gradient formed encourages silver ions from outer layer 122 to migrate away from metal 140, nevertheless silver ions are transported into absorbent material 124 and against metal 140 by hydraulic action during use. These positive ions then will migrate away from metal 140 when liquid flow ceases, whereby the flux increases the permeation of ions throughout device 120 in a self sterilizing effect. The electric field exerted between outer layer 122 and metal 140 also exerts a killing effect on microbes after silver ions have been expelled outward from device 120. Outer layer 122 provides a contiguous positive electric potential that repels organic compounds, and has a catalytic self-cleaning action that aggressively binds oxygen with free silver ions (not shown) and breaks hydrogen and sulphuric bonds in organic compounds. The separation of outer layer 122 and metal 140 is desirable in this embodiment as it insures a relatively even voltage gradient inside device 120 and upon the exterior of outer layer 122, thereby assuring that all portions of the device operate at similar voltage and current levels.

Device 120 is designed for use on a surface 26 of body 27, and also in body cavities and regions of the type described above with respect of the multi-layer roll of FIG. 5. Thus, device 120 may have a wide range of configurations including without limitation cylindrical, cubic and spherical. Device may also be used in applications such as those described below in regard to device 520.

Considering next the use and operation of device 220 illustrated in FIG. 7, this embodiment of the invention is intended for use in body cavities and regions such as those discussed above with respect to device 120. Because the silver-bearing material of outer layer 222 is in direct contact with metal 240, electrolytic dissociation of metal ions from both the outer layer (one electrode) and the metal (the other electrode) occurs and galvanic coupling of the short circuited electrode pair occurs to body 27. causing a dispersion of weak electrical fields about, and from, device 220. This results in the delivery of metallic ions in a therapeutic concentration. The concentration of metal ions is predisposed to remain constant for a period of time until the available metal of the electrode materials is substantially diminished.

Regarding use and operation of device 320 illustrated in FIG. 8, this device is designed for insertion in the same body cavities and regions as those described above with respect to device 120. The operation of device 320 is substantially identical to the operation of device 20, as described above.

Device 420 is designed for use on a surface 26 of body 27, as described above with respect to device 20. The spaced placement of first region 421 (the anode) and second region 438, (the cathode) create an ion pathway (indicated by arrows in FIG. 9) through the body 27 to deliver drugs or agents created by these regions or that are held in reservoirs 460 and 462. At second region 438 (the cathode) of device 420 hydroxl (OH) and hydrogen (H) are produced, and at first region 421 (the anode) hydrogen (H) and chlorine (Cl) are produced. The chlorine is an acid that further promotes dissociation of silver ions from the anode material. Between the electrode pair water and oxygen form that provide therapeutic benefits. These byproducts are not toxic in the concentrations formed and assist repair of tissue.

Device 520 differs in its intended application from the other devices of the present invention in that in addition to being usable for wound therapy, or it may also be used as a surface cleaning device not designed for wound healing. In this latter application, the silver and metal 540 are provided principally for their antibacterial, antifungal and antiviral properties. Thus, a typical application for device 520 is as a kitchen sponge used for dishwashing, counter cleanup and other routine kitchen clean up tasks. Additionally. the device can be used in hospitals, operating rooms. field medical kits, restaurants, laboratories, or in situations that require cleaning of potential pathogens from surfaces. such as on farms, or in bioweapon theaters of engagement. Furthermore, device 520 can be used as a mass compress dressing for wound hemostasis, high absorption of liquids, and safe control of microbes. Because of the radio opaque nature of metals, a further use is as a non-toxic surgical sponge that can be detected by X rays to avoid accidental loss in the body. Yet another application of device 520 is as a feminine napkin.

Use of the embodiment featuring pieces of silver and metal 40 in a viscous matrix proceeds in the same manner one uses lipstick, lip balm, sunscreen or other lotions, plasters and salves. Ion generation and transport occurs as described above.

An important advantage of all embodiments of the present invention is that they provide therapeutic and/or antibacterial, antifungal and antiviral properties without the need for an external power source. This reduces the cost of devices, simplifies uses and enhances reliability.

As compared to known wound healing and silver ion producing devices that do not feature an external power source, the present invention typically provides a higher concentration of silver ions than known devices. This is achieved through use of high total surface area materials in combination with dissimilar metals such as zinc. The present invention also offers optional delivery of the non-silver metal as well as other drugs and agents.

It is understood that the specification and drawings are illustrative of, but do not limit, the present invention, and other embodiments and variations are within the spirit and scope of the present invention.

What is claimed is:

1. An electrolytic device, comprising:
   a) a structure having a first surface with a first surface area, a thickness region and a plurality of openings in said thickness region, said plurality of openings being defined by a plurality of inner surfaces that together have an inner surface area, wherein said plurality of inner surfaces comprise silver; and
   b) a metal-bearing material other than silver interspersed throughout at least some of said plurality of openings.

2. An electrolytic device according to claim 1, wherein said structure comprises a single element.

3. An electrolytic device according to claim 1, wherein said structure comprises a sheet of foil.

4. An electrolytic device according to claim 1, wherein said structure comprises a sponge.

5. An electrolytic device according to claim 1, wherein said structure comprises polymeric material.

6. An electrolytic device according to claim 1, wherein said structure comprises a filament.

7. An electrolytic device according to claim 1, wherein said structure comprises a plurality of elements.

8. An electrolytic device according to claim 7, wherein said plurality of elements includes fibers.

9. An electrolytic device according to claim 8, wherein said fibers are combined together to form a fabric layer.

10. An electrolytic device according to claim 9, wherein said fabric layer is made from polyimid coated with silver.

11. An electrolytic device according to claim 9, wherein said plurality of elements comprise polymeric material.

12. An electrolytic device according to claim 8, wherein said fibers are aggregated together.

13. An electrolytic device according to claim 7, wherein said plurality of elements includes a plurality of sheets of foil.

14. An electrolytic device according to claim 1, wherein said metal-bearing material physically dissociates when exposed to moisture.

15. An electrolytic device according to claim 1, wherein said metal-bearing material other than silver releases ions when exposed to moisture.

16. An electrolytic device according to claim 1, wherein said metal-bearing material other than silver comprises zinc oxide.

17. An electrolytic device according to claim 1, wherein said metal-bearing material other than silver is selected from the group consisting of aluminum, cobalt, copper, gold, iron, magnesium, platinum, titanium and zinc, and oxides thereof.

18. An electrolytic device according to claim 1, wherein said metal-bearing material other than silver is in the form of powder.

19. An electrolytic device according to claim 1, wherein said first surface area and said inner surface area together equal at least 1.1 times said first surface area.

20. An electrolytic device according to claim 1, wherein said first surface area and said inner surface area together equal at least 2 times said first surface area.

21. An electrolytic device according to claim 1, wherein said structure further comprises a body contacting surface and an opposite surface and said body contacting surface and said opposite surface are essentially flat.

22. An electrolytic device according to claim 1, wherein said structure further comprises a body contacting surface and an opposite surface and said opposite surface includes a plurality of recesses.

23. An electrolytic device according to claim 1, wherein said metal other than silver is present at said body contacting surface.

24. An electrolytic device according to claim 1, further comprising a body contacting surface, an opposite surface and a barrier layer proximate said opposite surface.

25. An electrolytic suture device according to claim 24, wherein said barrier layer includes at least one port for transporting fluid.

26. An electrolytic device according to claim 1, wherein said structure is rolled about a central axis so as to form a multilayer cylinder.

27. An electrolytic device, comprising:
   a) a structure having a first surface with a first surface area, a thickness region and a plurality of openings in said thickness region, said plurality of openings being defined by a plurality of inner surfaces that together have an inner surface area, wherein said first surface and said plurality of inner surfaces comprise silver; and
   b) a metal-bearing material other than silver that contacts said first surface.

28. An electrolytic device according to claim 27, wherein said structure comprises an interior region and said metal-bearing material other than silver is disposed in said interior region.

29. An electrolytic device according to claim 27, wherein said structure comprises a sponge-like material.

30. An electrolytic device according to claim 27, wherein said metal-bearing material other than silver is chosen from the group consisting of aluminum, cobalt, copper, gold, iron, magnesium, platinum, titanium and zinc, and oxides thereof.

31. An electrolytic device according to claim 27, wherein said metal-bearing material other than silver is in tablet form.

32. An electrolytic device according to claim 27, wherein said metal-bearing material other than silver physically dissociates when exposed to moisture.

33. An electrolytic device according to claim 27, further including an absorbent material.

34. An electrolytic device according to claim 33, wherein said metal-bearing material other than silver is freely disposed in said absorbent material such that said metal-bearing material other than silver contacts said structure.

35. An electrolytic device according to claim 34, further comprising a medicament disposed in said absorbent material.

36. A device according to claims 27, further including an abrasive layer attached to said structure.

* * * * *